United States Patent [19]
Wickens et al.

[11] Patent Number: 5,985,575
[45] Date of Patent: Nov. 16, 1999

[54] TETHERED FUNCTION ASSAY FOR PROTEIN FUNCTION

[75] Inventors: Marvin P. Wickens, Madison, Wis.; Roy Parker, Tucson, Ariz.

[73] Assignees: Wisconsin Alumni Research Foundation, Madison, Wis.; The Arizona Board of Regents on behalf of the University of Arizona, Tucson, Ark.

[21] Appl. No.: 09/081,731

[22] Filed: May 20, 1998

[51] Int. Cl.⁶ .............................. C12Q 1/68; C07K 16/00; C07H 21/04
[52] U.S. Cl. ........................ 435/6; 536/24.1; 530/388.21
[58] Field of Search ................................ 435/6; 536/24.1; 530/388.21

[56] References Cited

PUBLICATIONS

D.J. Sengupta, et al., "A Three–Hybrid System to Detect RNA–Protein Interactions In Vivo," *Proc. Natl. Acad. Sci. USA* 93:8496–8501, 1996.
C. Southgate, et al., "Activation of Transcription by HIV–1 Tat Protein Tethered to Nascent RNA Through Another Protein," *Nature* 345(6276) :640–642, 1990.
R. Stripecke. et al., "Proteins Binding to 5' Untranslated Region Sites: A General Mechanism for Translational Regulation of mRNAs in Human and Yeast Cells," *Mole. Cell. Biol.* 14(9) :5898–5909, 1994.
J. Valcárcel, et al., "The Protein Sex–Lethal Antagonizes the Splicing Factor U2AF to Regulate Alternative Splicing of Transformer Pre–mRNA," *Nature* 362:171–175, 1993.
M. Wickens, et al., "Translational Control of Developmental Decisions," *Translational Control*, Cold Spring Harbor Laboratory Press, pp. 411–450, 1996.
M. Wickens, et al., "Life and Death in the Cytoplasm: Messages from the 3' End," *Curr. Opin. Genet. & Develop.* 7:220–232, 1997.
Paraskeva et al., Proc. Natl. Acad. Sci. USA, 95(3), 951–956, Feb. 1998.

*Primary Examiner*—Robert A. Wax
*Assistant Examiner*—Maryam Monshipoouri
*Attorney, Agent, or Firm*—Quarles & Brady LLP

[57] ABSTRACT

A method for determining the function of a test protein is disclosed. In a preferred embodiment, this method comprises the steps of fusing a test protein to an RNA-binding protein and exposing the fusion protein to recombinant reporter mRNA molecule that comprises a binding site for the RNA-binding protein in the 3' untranslated region. One then observes the properties of reporter mRNA and correlates the reporter properties with test protein function.

19 Claims, 14 Drawing Sheets

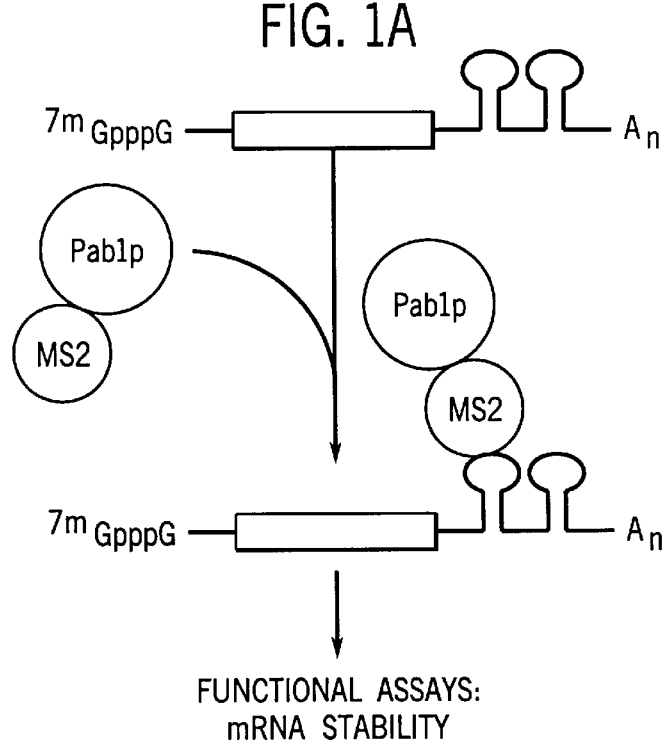
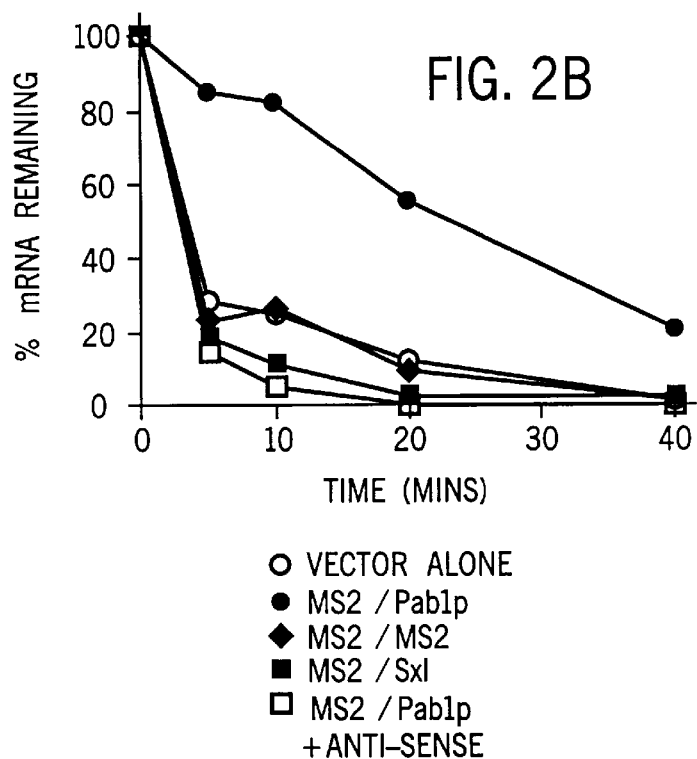

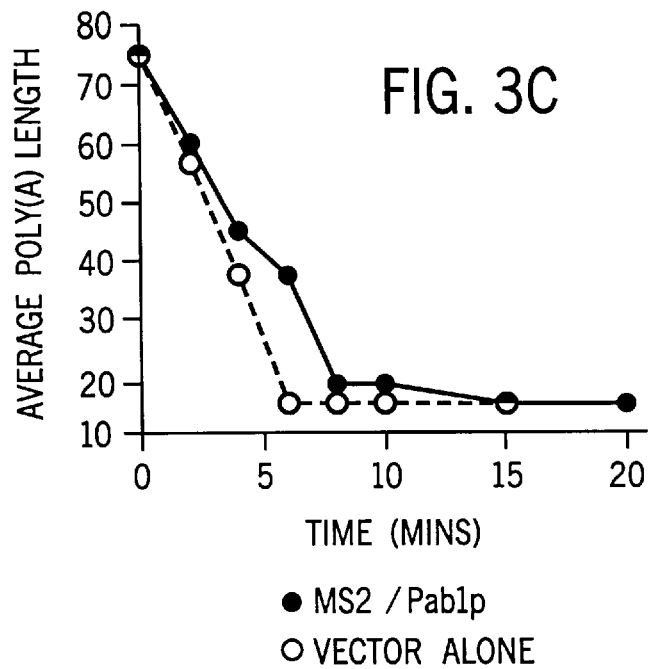
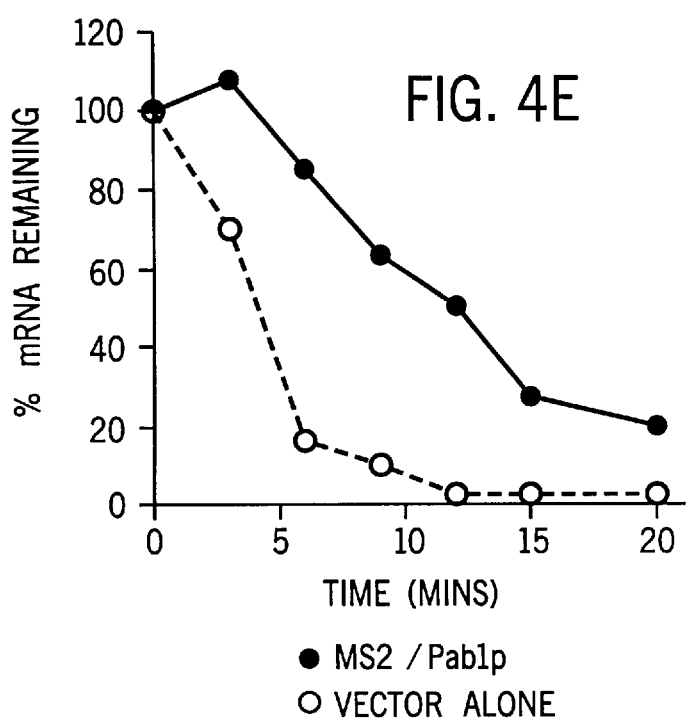

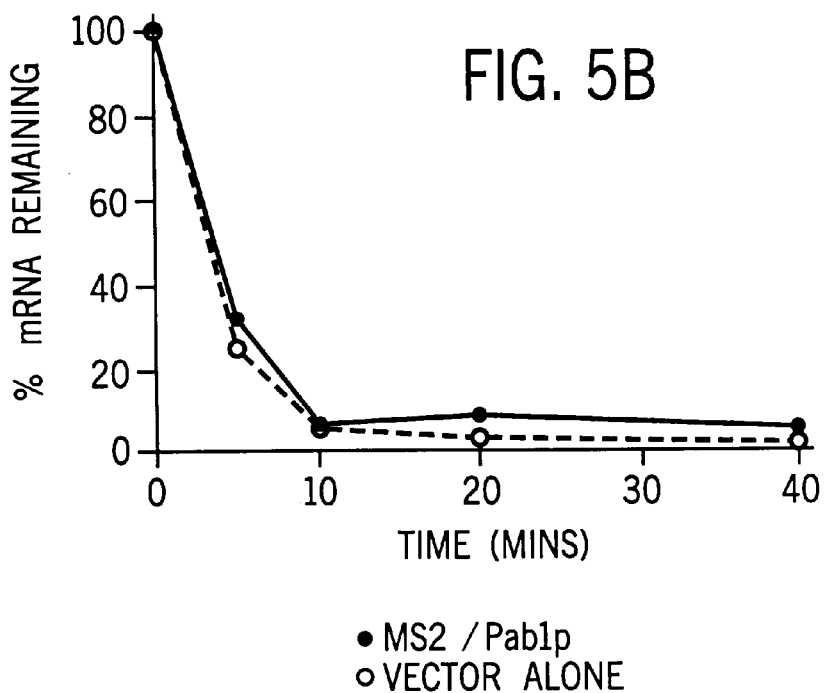
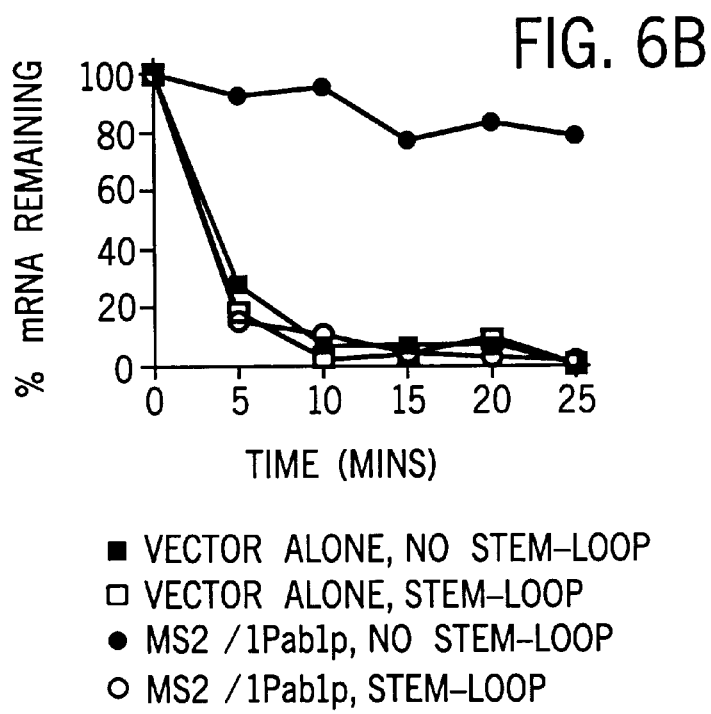

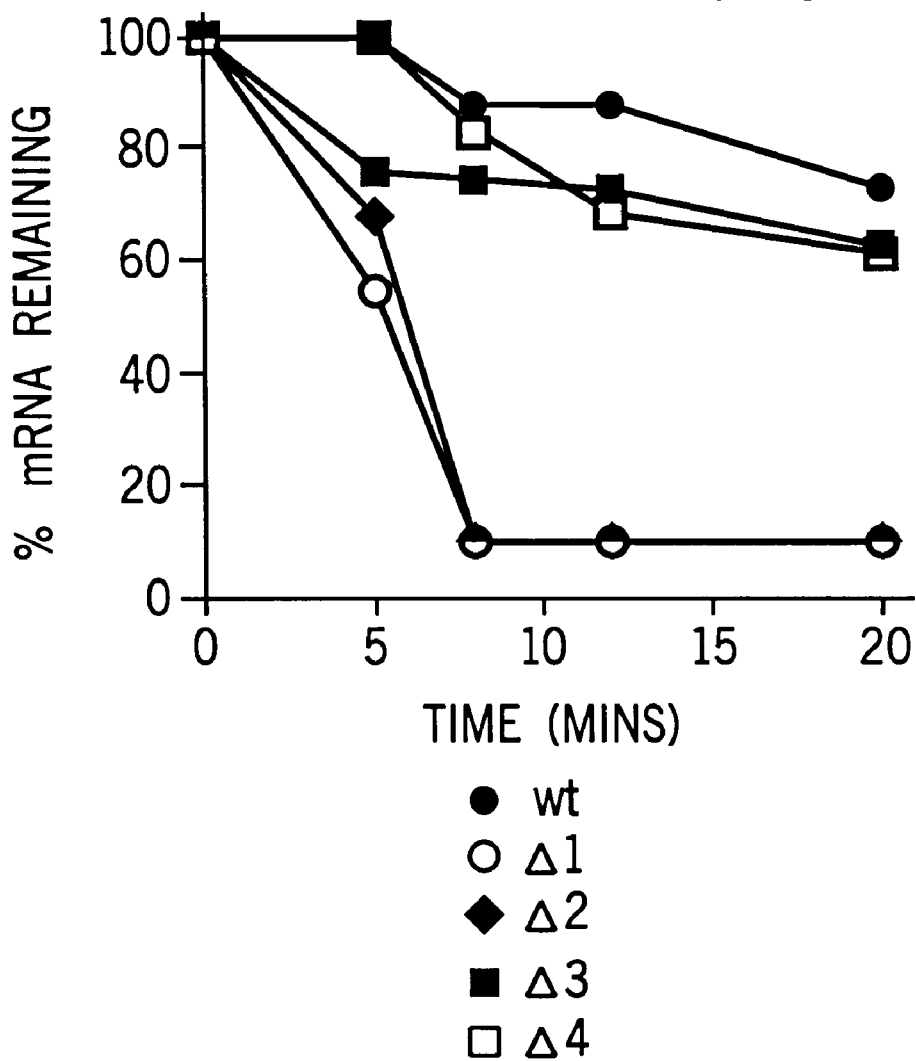

TETHERED FUNCTION ASSAY FOR PROTEIN FUNCTION

CROSS-REFERENCE TO RELATED APPLICATION

Not applicable.

STATEMENT REGARDING FEDERALLY SPONSORED RESEARCH OR DEVELOPMENT

Not applicable.

BACKGROUND OF THE INVENTION

The biological function of nucleic acid binding proteins is often separable from their sequence specificity. In some cases, as with many RNA and DNA polymerases, a protein possessing the enzymatic activity site is directed to the correct location through its interaction with a distinct polypeptide. In others, as with many transcription factors and regulators of mRNA metabolism, function and sequence specificity reside in distinct domains of the same polypeptide. Dissection of the two domains from one another facilitates their detailed analysis, liberating each from the constraints of the other.

Poly(A) is a virtually universal feature of mRNAs in eukaryotes, and exists in the cytoplasm as an RNA-protein complex with Poly(A) binding protein (Pab1p). Like the tail, Pab1p is highly conserved. The presence of a poly(A) tail typically stabilizes mRNAs and can enhance their translation both in vivo and in vitro. It is unclear whether these biological functions reside solely in the protein, or require the RNA-protein complex.

The role of the Pab1p in stability has been demonstrated in the budding yeast *Saccharomyces cerevesiae*. The yeast PAB1 gene is required for viability (Sachs, 1986). The lethality of a pab1 deletion can be suppressed by mutations within various genes associated with mRNA turnover, such as xrn1 and dcp1, indicating Pab1p likely has an essential function in mRNA decay (Hatfield, 1996). Degradation of most yeast mRNAs is initiated by shortening of the 3' poly(A) tail, followed by Dcp1p cleavage of the 5'm$^7$GpppG cap ("decapping"), which permits 5' to 3' exonucleolytic digestion by the XRN1 gene product (Decker, 1993; Muhlrad, 1994; Beelman, 1996). Decapping occurs only after the poly(A) tail has been shortened to 10–12 adenosine residues (Muhlrad, 1994), which corresponds provocatively with the minimal Pab1p binding site of 12 adenosines and suggests that eviction of the last Pab1p/poly(A) complex triggers turnover. Furthermore, in the absence of Pab1p, decapping becomes independent of poly(A) length (Caponigro, 1995).

The molecular link between poly(A) and the cap may be a tripartite protein bridge between the two ends of the mRNA. Pab1p, when bound to the poly(A) tail, interacts in vitro with two yeast proteins, TIF4631 and TIF4632, related to the translation initiation factor eIF-4G (Tarun, 1996). eIF-4G in turn interacts with eIF-4F, containing the cytoplasmic cap-binding protein, eIF-4E, an initiation factor itself. The in vitro association of Pab1p and eIF-4G is dependent on the poly(A) tail, and is consistent with earlier work demonstrating biochemical interactions between poly (A) and complexes containing eIF-4F in vitro (Gallie, 1994). The same tripartite bridge could explain poly(A)'s stimulation of translation in vitro and in vivo.

The interaction between Pab1p and eIF-4G, demonstrated in vitro, requires the presence of RNA, implying that the poly(A)/Pab1p complex likely is essential. Similarly, deadenylation in crude yeast extracts is dependent on the presence of Pab1p, implying that the yeast deadenylase may recognize not poly(A) alone, but the poly(A)/Pab1p complex (Lowell, 1992).

BRIEF SUMMARY OF THE INVENTION

In one embodiment, the present invention is a method for determining the function of a test protein. In a preferred form of this method, one first fuses a test protein to an mRNA binding protein, preferably by first creating a chimeric gene sequence encoding both proteins in tandem. One then exposes the fusion protein to a recombinant reporter mRNA molecule under conditions suitable for the binding of the fusion protein to the reporter mRNA. The mRNA molecule comprises a binding site for the RNA-binding protein in the 3' untranslated region. Once the fusion protein is bound (or "tethered") to the reporter mRNA, one observes the properties of the reporter mRNA and correlates these properties with test protein function.

In a preferred form of the present invention, the RNA-binding protein is MS2 coat protein and the RNA-binding site is MS2 binding site.

In another preferred form of the present invention, the tethering takes place in yeast.

In a preferred form of the invention, a candidate inhibitor or enhancer compound is evaluated by exposing the compound to the tethered molecules.

Another form of the present invention is a tethered structure comprised of the reporter mRNA and fusion protein described above.

The present invention is also the tethered structure formed by binding between the fusion protein and the reporter mRNA.

It is an object of the present invention to analyze the function of a test protein by tethering the test protein to a reporter mRNA.

It is another object of the present invention to analyze candidate inhibitors and enhancers.

It is an advantage of the present invention that one need not know the natural RNA-binding sites of the test protein to analyze the protein's function.

Other objects, advantages and functions of the present invention will become apparent after one has reviewed the specification, claims and drawings herein.

BRIEF DESCRIPTION OF THE SEVERAL VIEWS OF THE DRAWINGS

FIG. 1A is a diagram of the experiment strategy described in the Examples.

FIG. 2 demonstrates mRNA stability conferred by MS2/Pab1p tethered to the 3' UTR. FIG. 2B quantifies the results of FIG. 2A.

In FIG. 3A RNA was prepared from a strain containing MS2/Pab1p. In FIG.

3B RNA was prepared from a strain containing the protein vector.

FIG. 4 demonstrates that tethered Pab1p stabilizes mRNAs that do not receive a tail. FIG. 4E is a quantitation of results of the other panels.

FIG. 5 demonstrates that tethered Pab1p does not prevent decay through mRNA surveillance. FIG. 5B is a quantitation of results of FIG. 5A.

FIG. 6B is a quantitation of the results.

FIG. 7 shows that mRNA stabilization and poly(A) binding by Pab1p are genetically separable. FIG. 7B is a quantitation of the results of FIG. 7A.

DETAILED DESCRIPTION OF THE INVENTION

1. In General

Figure 1B:
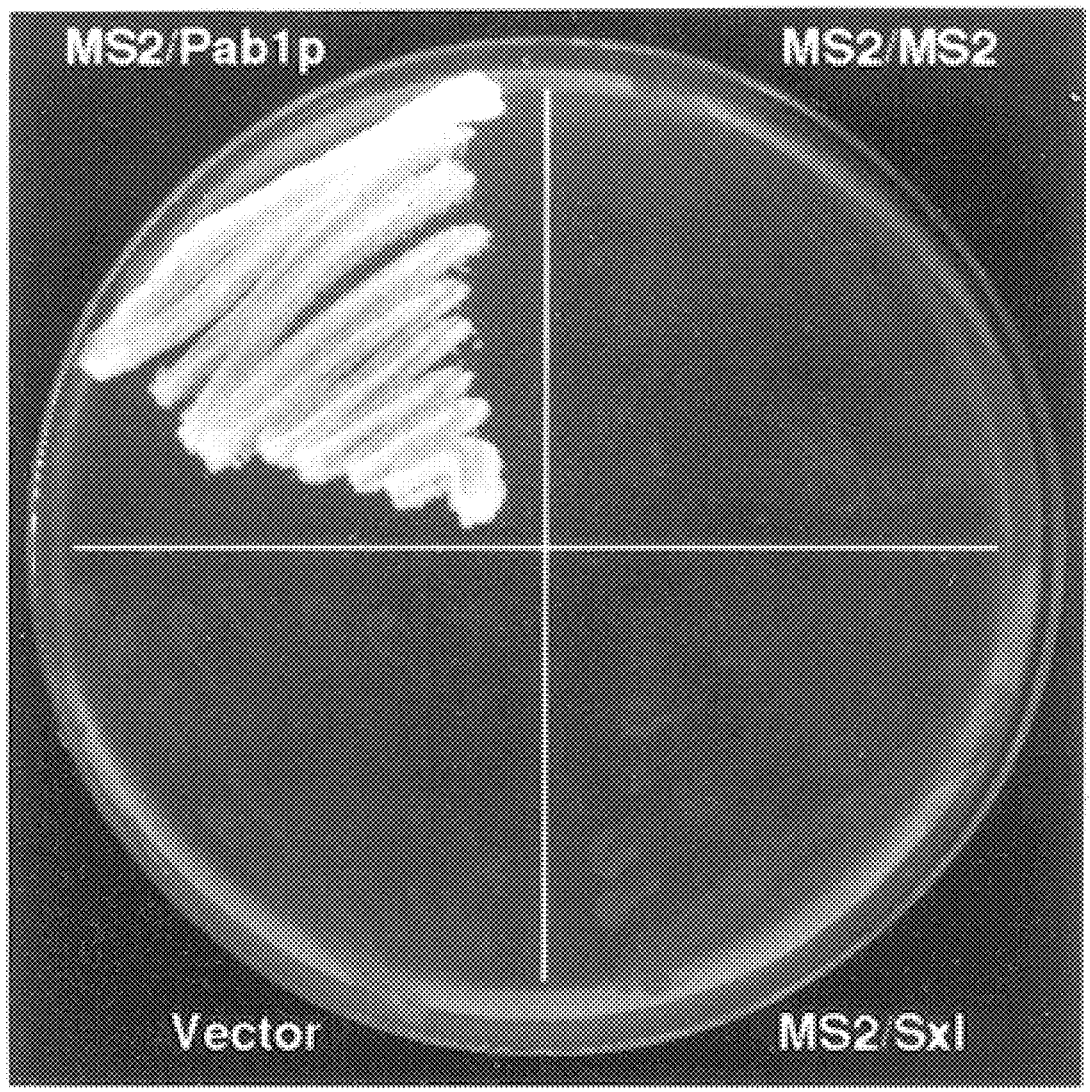
FIG. 1B is a photograph of a yeast selection plate following 5-FOA selection. The data demonstrate that the fusion protein is functional and can provide the essential function of Pab1p in yeast.

The present invention is a method of analyzing the function of a test protein by "tethering" the test protein to a reporter mRNA. By "tethering" we mean attaching the test protein to a reporter mRNA by the use of an mRNA binding protein and binding site.

The results of our experiments described below in the Examples have allowed us to disclose a generalized method suitable for any test protein. The Examples below demonstrate use of the tethered function approach to analyze the function of the Pab1p protein. We demonstrate in the Examples that the effect of the poly(A) tail on MRNA stability in vivo is mediated largely, if not entirely, by the protein to which it binds, poly(A) binding protein (Pab1p). Further, stabilization by Pab1p requires ongoing translation.

To examine Pab1p function in vivo, we tethered Pab1p to the 3' UTR of reporter mRNAs by fusing Pab1p to MS2 coat protein and placing MS2 binding sites in the 3' UTR of the reporter mRNA.

Similarly, the tethered function approach of the present invention provides a general assay for the function of mRNA-binding proteins without prior knowledge of the RNA sequences with which they interact. In one embodiment, the present invention is a method for analyzing the function of a protein comprising a first step of fusing the test protein to an RNA binding protein and exposing this fusion to a recombinant reporter RNA molecule. The reporter RNA molecule comprises a binding site for the RNA binding protein in the 3' UTR. The fusion protein binds to the RNA binding protein, and one then observes and analyzes the properties of the reporter mRNA. Typically, these "properties" will include stability, translatability or location.

2. Creation of the Fusion Protein

Applicants envision that the test protein/RNA binding protein fusion may be made by many methods known to those of skill in the art. In the Examples below, a fusion protein comprised of Pab1p and the MS2 coat protein was created by creating a gene construct encoding the proteins in tandem. Creating fusion proteins is typically practiced by recombinant DNA methods. In the present invention, either protein may be first or last.

By "in tandem," we mean that the gene construct encodes the two proteins in a sequential manner. The coding regions are not necessarily directly connected. One might wish to insert a linking protein sequence between the two proteins.

Preferably, one would wish to ascertain that the test protein and the RNA-binding protein are in a native conformation. Although it is desirable to know that the test protein is in a native state, it is a difficult procedure for a protein of unknown function. However, one may check that the test protein is being produced and that the RNA-binding portion is functional. The Examples below describe evaluation of the test protein by measuring binding of the fusion protein to MS2 RNA sites in vitro and by Western blotting to anti-MS2 coat antibodies. In some applications (as with Pab1p), one can approximate whether the protein is folded correctly by asking whether it can rescue the phenotype of the appropriate mutant in yeast.

An RNA binding protein of the present invention is any protein capable of binding a specific binding site placed within the 3' UTR of a reporter mRNA. One preferable example is the MS2 coat protein/MS2 binding site pair described below in the Examples. Of course, other suitable pairs exist, such as IRE and IRP (Iron-Response Element and Iron Regulatory Protein), histone 3' stem-loop and SLBP (stem-loop binding protein), and HIV and BIV TAR and Tat.

Any new candidate tethering function can be tested by combining the candidate with a protein of known function, such as Pab1p.

The affinity of the tethering protein for its target is likely an important variable; MS2 coat protein binds to the particular target we have used with approximately 1 nM affinity in a cell-free system. The other protein/RNA combination listed above bind even tighter than that in vitro.

A second consideration is whether the protein can be expressed in yeast at reasonable levels, sufficient to be useful phenotypically. We mention the specific examples above because they are cases in which the RNA/protein combination can be created in yeast and be functional in RNA binding. For example, we know that IRP, expressed as a fusion protein with a transcription activation domain, binds to an IRE in yeast.

3. Exposure of the Fusion Protein to the Reporter mRNA

Once the fusion protein has been created, the next step is to expose the fusion protein to a recombinant reporter MRNA. The reporter mRNA of the present invention has a RNA protein binding site added to the 3' UTR. By "recombinant" reporter mRNA, we mean that the RNA-binding site does not naturally occur in the 3' UTR of the reporter RNA molecule.

One of skill in the art would recognize that standard molecular biological methods may be used to insert a suitable RNA-binding site, such as the MS2 binding site described below in the examples, into the RNA molecule. For example, one might create a chimeric gene encoding the mRNA with a DNA sequence encoding the RNA-binding site inserted into the 3' UTR.

A reporter mRNA of the present invention is one in which the mRNA and/or its product protein may be conveniently monitored. A typical example is the MFA2-MS2 RNA described below in the Examples. MFA2 mRNA was chosen because the mRNA is among the least stable in yeast, with a half-life of approximately 4 minutes. This mRNA would, of course, be especially suitable for applications where one wishes to evaluate the effect of a test protein on mRNA stability.

The reporter one chooses will depend on precisely what one wishes to assay. For example, in the Examples below we wanted to test whether tethered Pab1p would stabilize the MRNA. To do that, we had to use as a reporter an mRNA that was unstable. If a stable mRNA were chosen, one would not be able to see more stabilization. We chose MFA2 mRNA, one of the least stable in yeast for the that purpose (see D. Muhlrad, et al., *Genes & Dev.* 8:855–866, 1994). Conversely, if one wanted to look at (or screen for) proteins that caused instability when tethered to the 3' UTR, one would need to start with a stable reporter (such as PGK1 in yeast, see C. Decker and R. Parker, *Gene & Dev.* 7:1632–1643, 1993).

Similarly, if one wanted to determine whether the protein repressed translation, one would want to use a reporter whose translation can be readily monitored, such as LacZ, luciferase or a selectable marker, such as HIS3, URA3, or CUP1. The latter reporters provide a phenotypic selection for expression of the gene. If one is screening a library, one would need a selection of that type.

Finally, if one wishes to screen for proteins that affected mRNA localization, one would ideally use a reporter that produced a protein whose location in the cell can be determined easily. GFP (green fluorescent protein) is an example of a suitable reporter for this screen (P. Takizawa, et al., *Nature* 389:90–93, 1997).

In summary, the reporter one uses needs to be designed to suit the purposes one has in mind. If one wants to screen a library for proteins that could have any of several functions, then one needs a battery of reporters. These could be present in a single strain or assays successfully using multiple strains.

One then exposes the reporter mRNA to the test protein under conditions in which the reporter mRNA and test protein are "tethered" to each other. The Examples below describe suitable conditions in yeast, although we envision that many other conditions are possible.

To practice the present invention, one needs to introduce the DNA encoding the protein, as well as the reporter, into a cell. Yeast is one system where this is readily possible. It is also possible by transfection of cultured cells and by infection of cultured cells with viral vectors. Any system that permits the introduction and expression of cloned DNA would be suitable.

In a library screen, one would prefer to monitor the function of tethered proteins by phenotype, using a selection such that only those cells containing the function will grow. For example, one could start with an unstable mRNA encoding, for example, CUP1. One would transform in the MS2 coat protein fusion library, then select for higher levels of copper resistance. Positives would be screened using other reporter mRNAs. If one wanted to identify proteins that affected localization, one would typically transform the library into a GFP reporter strain and would then screen visually under the microscope for localized GFP.

For any particular known protein, one could introduce the appropriate fusion protein gene with the reporter and do assays with that strain. For example, if one wanted to identify inhibitors of a protein's ability to stabilize mRNAs, one would introduce that protein into a yeast (or mammalian) cell that carried the reporter. One would then introduce candidate inhibitors and monitor stabilization. However, one would miss proteins that, for one reason or another, could not function in yeast.

4. Analysis of Reporter mRNA

The attributes or properties of the reporter mRNA are indicative of the function of the test protein. For example, the test protein could be found to prolong or stabilize the reporter mRNA.

To measure mRNA turnover rates in vivo, we used a transcriptional pulse chase protocol described below in the Examples. As described below, cells were grown in glucose, then induced briefly in galactose to induce transcription. After 10 minutes, transcription was repressed by addition of glucose and by thermal inactivation of a temperature sensitive allele of RNA polymerase too. The decay of the newly synthesized mRNA could be monitored by northern blotting. We showed below that our MS2/Pab1p fusion protein dramatically and specifically stabilized the reporter mRNA by exposing the tethered molecules to test compounds.

One may wish to examine the reporter mRNA for other criteria. The biological function to be assayed may be any involved in mRNA or pre-mRNA metabolism or regulation. The function thus includes, but is not confined to, mRNA stabilization, mRNA destabilization, translational activation, translational repression, mRNA localization and mRNA processing.

Proteins that function naturally by binding to sites in the 3' UTR are clear and important candidates for this analysis. Proteins that bind to the 3' UTR have been identified already that promote each of the biological functions above. Although the majority of such proteins have not yet been identified, their existence is clear through identification of their RNA binding sites.

Although proteins that bind to the 3' UTR will be detected and assayed using the method, proteins that bind elsewhere, or not at all, to a specific mRNA binding site will also be accessible. These include proteins that are components of the machinery that execute (rather than regulate) any of the step in mRNA production or function. For example, a protein involved in recruiting ribosomes to all mRNAs (i.e., a translation factor), would be detected, even though it might never actually contact the mRNA in a natural cell. Similarly, a nuclease that is naturally recruited to an mRNA through its interaction with an mRNA-bound protein would, in the tethered function assay, cause rapid decay of the mRNA to which it is bound. Likewise, proteins whose natural binding sites lie elsewhere (i.e., in the 5' UTR, open reading frame, or in introns) would all be amenable to analysis.

The method would not detect proteins that must bind to their specific natural binding site in order to function. A requirement for binding to the natural binding site could arise either because the binding of the protein results in a specific RNA-protein complex that exerts the function. Alternatively, such a requirement could arise because the protein must be bound at a specific location in the mRNA or pre-mRNA (for example, at a fixed distance from another RNA sequence).

5. Applications

We envision the following as specific applications for the tethered function analysis method:

a. Identifying inhibitors or enhancers of the function of any RNA binding protein The method of the present invention could be used to evaluate inhibitors or enhancers of RNA binding protein functions by inserting a candidate compound into the tethered function analysis. An advantage of this method is that it does not require knowledge of the protein's RNA binding site because an artificial tether would be used. Any function may be analyzed, such as stability, translation, transport and packaging of viruses. Inhibitors or enhancers could be peptides, proteins or small molecules.

b. Genomic analysis of RNA-binding proteins

The present invention could be used for genomic analysis of RNA binding proteins by screening genomic protein libraries for naturally occurring proteins that participate in any form of post-transcriptional control or screening synthetic peptide libraries for proteins that can specifically regulate an mRNA to which they are tethered.

The method would allow one to define new proteins or peptides by function, independent of their RNA binding specificity, and define new families of regulatory proteins, providing new targets for therapeutics.

C. RNA-protein linkage map

The present invention would also allow one to identify all interacting RNA and protein partners and identify the functions of the protein partners.

d. Assay of RNA-protein interaction

One primary utility of the present invention would be to analyze RNA-protein interactions. The method relies on the binding of the protein to its natural site, linking to a protein of known function, such as PAB.

The present invention could be used to do exactly what is done by the three hybrid system (see U.S. Pat. No. 5,677,131; incorporated by reference) but with the second hybrid protein now consisting of MS2 linked to Pab1p, and the target being the reporter mRNA protein binding sites, rather than the "hybrid" RNA. When an interaction occurs, the mRNA will be stabilized because we know that tethered Pab stabilizes mRNA. This results in a phenotypic assay for the RNA-protein interaction per se. Therefore, if one had a candidate RNA sequence, one could insert it into the 3' UTR and screen a library of cDNAs linked to Pab. Likewise, if one had a protein that one wished to find the target for, one could create a library of sequences in the 3' UTR of the reporter and then introduce the test protein linked to Pab1p.

One might identify a protein target when the RNA is known or identify an RNA target when the protein is known. This application would be especially useful to identify viral packaging and replication sites and proteins genetically implicated in disease. The method permits greater flexibility in length of RNA than now possible in the three-hybrid system (See U.S. Pat. No. 5,677,131).

In another embodiment, the method would enable one to screen for inhibitors and develop pharmaceuticals with RNA binding as the target. Examples of processes in which this screening could be utilized are viral packaging and replication, and cellular mRNAs and their control.

The present invention also enables one to identify novel RNA ligands in vivo with the goal of developing, for example, new pharmaceuticals. The method could be complementary to current test tube selection schemes.

EXAMPLES

We demonstrate herein that Pab1p alone is sufficient to stabilize mRNAs in vivo, and that this process requires translation. These results imply that the role of the poly(A) tail is passive, serving only to recruit Pab1p. To uncouple analysis of Pab1p function from the presence of a poly(A) tail, we tethered the protein to the 3' UTR of a reporter mRNA using a well-known RNA-protein interaction. This strategy is useful in identifying and dissecting proteins that regulate mRNA biogenesis and function.

A. Results

1. Experimental strategy

Poly(A) binding protein is essential in yeast (Sachs, 1986). To assess Pab1p function independent of effects on viability, we exploited the strategy diagrammed in FIG. 1. FIG. 1A diagrams the assay. To uncouple analysis of Pab1p function from the presence of a poly(A) tail, Pab1p was tethered to the 3' UTR of reporter mRNAs by fusing it to MS2 coat protein and placing MS2 binding sites in the 3' UTR of the reporter. For simplicity, a single bound protein molecule is depicted; however, since MS2 coat protein binds as a dimer, at least two MS2/Pab1p molecules are likely bound per site.

Referring to FIG. 1, a chimeric protein consisting of MS2 bacteriophage coat protein linked to yeast Pab1p (MS2/Pab1p) was expressed in yeast that carried a reporter mRNA bearing MS2 recognition sites within its 3' UTR. Two recognition sites were inserted, as binding of MS2 coat protein is cooperative. The approach separates analysis of the function of Pab1p from its ability to bind poly(A) or to support cell growth. Specifically, we determined whether mRNA stabilization in vivo was conferred by Pab1p alone, or by the Pab1p/poly(A) complex.

To use this strategy, it first was necessary to determine that the MS2/Pab1p fusion protein could provide Pab1p's normal essential function in vivo. To this end, we tested whether a gene encoding the MS2/Pab1p fusion protein could complement a pab1 deletion (Sachs, 1987). A plasmid carrying the wild-type PAB1 gene and a URA3 marker was introduced into yeast harboring a pab1 deletion. This strain was then transformed with a second plasmid expressing the MS2/Pab1p fusion or various control plasmids. Transformants were then analyzed on media containing 5-flourooratic acid (5-FOA), which selects for the loss of the URA3 plasmid that provided wild-type Pab1p. Cells expressing the MS2/Pab1p fusion protein grew on 5-FOA. In contrast, cells expressing fusion proteins in which MS2 coat protein was fused to the Drosophilia Sex-lethal protein (MS2/Sxl) or to another copy of MS2 coat protein did not support viability, nor did the parental expression vector. These observations demonstrate that the MS2/Pab1p fusion protein provides PAB1's essential function(s) in vivo.

2. mRNA stability is conferred by MS2/Pab1p tethered to the 3' UTR

To examine the effects of Pab1p on mRNA decay, we inserted MS2 coat protein recognition sites into the 3' UTR of MFA2 mRNA. This mRNA is among the least stable in yeast, with a half-life of approximately 4 minutes (Herrick, 1990). To measure mRNA turnover rates in vivo, we used a transcriptional pulse-chase protocol (Decker, 1993). Transcription of the MFA2/MS2 reporter mRNA was placed under control of the GAL1 promoter. Cells were grown in glucose, then incubated briefly in galactose to induce transcription. After ten minutes, transcription was repressed by addition of glucose and by thermal inactivation of a temperature-sensitive allele of RNA polymerase II (Nonet, 1987). The decay of the newly synthesized mRNA was then monitored by Northern blotting.

Figure 2A:
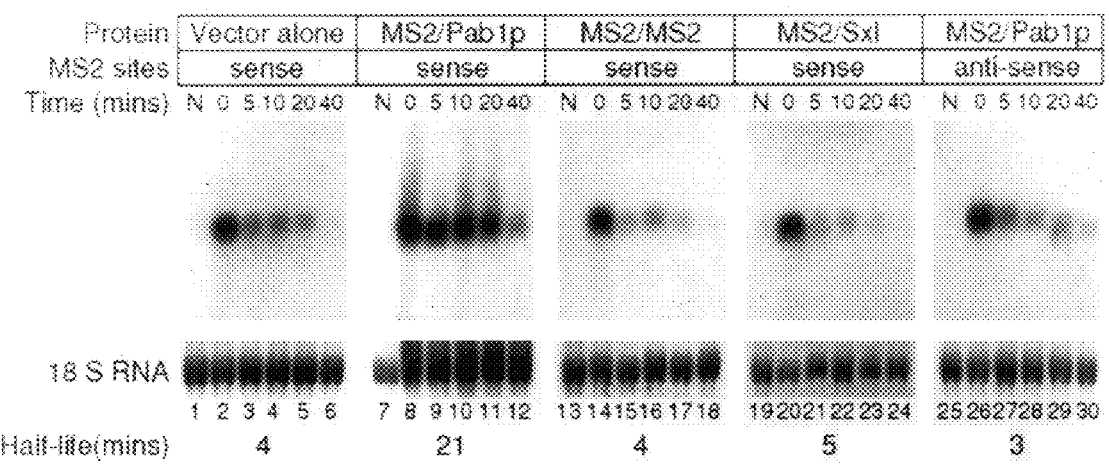
FIG. 2A is a chart comparing the decay of mRNAs in the presence of various combinations of protein and MS2 sites.

FIG. 2A demonstrates that mRNA stability is conferred by MS2/Pab1p tethered to the 3' UTR. FIG. 2A demonstrates the decay of mRNAs in the presence of MS2/Pab1p, analyzed by transcriptional pulse-chase experiments and Northern blotting. The RNA and protein present in each strain is indicated above each group of six lanes, as are the orientation of MS2 sites, and the time (in minutes) following transcriptional repression. "Vector alone" indicates strains not expressing a fusion protein, but still transformed with the parental protein vector. "N" indicates "not induced" sample taken prior to galactose induction. Half-lives are presented at the bottom of each panel.

FIG. 2B is a quantitation of results. Amounts of mRNA were normalized to the level of 18S rRNA, shown below each lane in Panel (A).

Figure 2C:
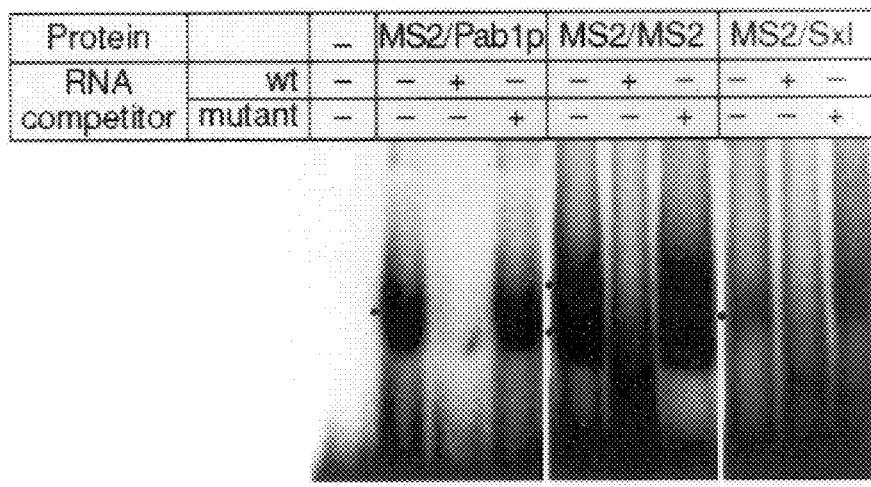
FIG. 2C is a diagram of the RNA binding activities of fusion proteins in yeast extract with various RNA competitors and protein present in each strain.

FIG. 2C demonstrates RNA binding activities of fusion proteins in yeast extracts. Gel retardation analyses were performed using crude extracts of yeast strains containing the proteins indicated above each group of lanes. The labelled RNA contains two MS2 coat protein recognition sites. The unlabelled competitor RNAs either contain high ("wt") or low ("mutant") affinity MS2 recognition sites. "Mutant" sites bind in vitro with a 100-fold reduction in affinity (Witherell, et al., 1991). Black dot is sown to the left of each group of 3 lanes to indicate position of specific complexes.

The MS2/Pab1p fusion protein dramatically and specifically stabilized the reporter mRNA carrying MS2 sites (FIGS. 2A–2B). mRNA half-life was increased from 4 to 21 minutes by the presence of the MS2/Pab1p fusion (FIG. 2A, lanes 1–12, FIG. 2B). This stabilization specifically required the Pab1p of the fusion protein: its replacement with either MS2 coat protein (FIG. 2A; lanes 13–18; "MS2/MS2") or the Drosophila Sex lethal (Sxl) protein (FIG. 2A, lanes 19–24; MS2/Sxl") eliminated the stabilization. Sxl protein and Pab1p both contain four RNA Recognition Motifs (RRMs) and are comparable in size, strongly suggesting that the Pab1p moiety is specifically required. mRNA stabilization is also specific with respect to RNA sequence: an mRNA in which the MS2 binding sites are in the antisense orientation is not stabilized by MS2/Pab1p (FIG. 2A, lanes 25–30). This result demonstrates that the effect of MS2/Pab1p operates only in cis, and that overexpression of the protein does not stabilize all mRNAs.

To ensure that each fusion protein was expressed and capable of RNA binding, we performed Western blotting and gel retardation experiments. Cross-reacting species of the expected size were observed in Western blotting experiments using an anti-MS2 coat protein monoclonal antibody to probe yeast extracts (gift of Dan Celander; data not shown). Moreover, in gel retardation experiments, each fusion protein present in yeast extracts formed complexes with RNAs carrying the MS2 recognition element; these complexes are specific as they are eliminated by the inclusion of excess unlabeled RNA containing the MS2 recognition elements, but not by an RNA containing elements with low affinity point mutations (FIG. 2C; Lowary, 1987).

We conclude that MS2/Pab1p bound to a 3' UTR stabilizes an otherwise unstable mRNA. Stabilization specifically requires the Pab1p portion of the molecule. For simplicity, we refer to the MS2/Pab1p molecule bound to the 3' UTR as "tethered Pab1p."

3. Tethered Pab1p stabilizes deadenylated mRNAs

Deadenylation rates are directly related to rates of mRNA decay in vivo (see Introduction). Thus, the tethered Pab1p could stabilize an mRNA either by effecting the rate of deadenylation or of its turnover subsequent to full deadenylation. To distinguish between these possibilities, we determined poly(A) lengths as a function of time in a transcriptional pulse-chase experiment. To do so, RNAs were separated in polyacrylamide gels, then analyzed by Northern blotting (FIG. 3).

FIG. 3 demonstrates that tethered Pab1p stabilizes deadenylated mRNAs but does not slow poly(A) removal. A transcriptional pulse-chase experiment was performed using strains carrying MS2/Pab1p or the comparable vecotr. RNAs were separated through a polyacrylamide gel to resolve different lengths of poly(A) tails. Time (in minutes) following transcriptional repression are given above each lane. Poly(A) tail lengths of the mRNAs are shown to the left of each panel; the position of the fully deadenylated RNA ($A_0$) was determined by RnaseH/oligo(dT) cleavage of the full-length reporter.

Figure 3A:
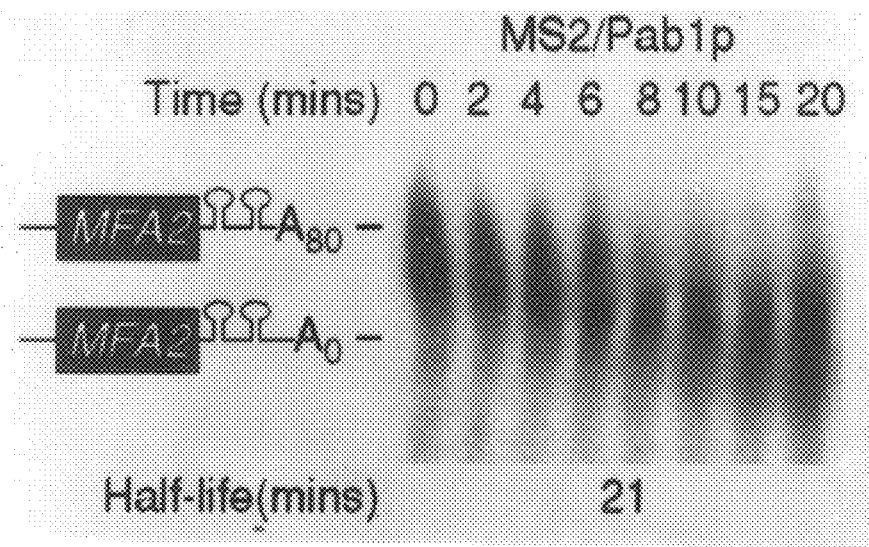
FIG. 3A demonstrates that tethered Pab1p stabilizes deadenylated mRNAs but does not slow poly(A) removal by transcriptional pulse-chase experiments.
Figure 3B:
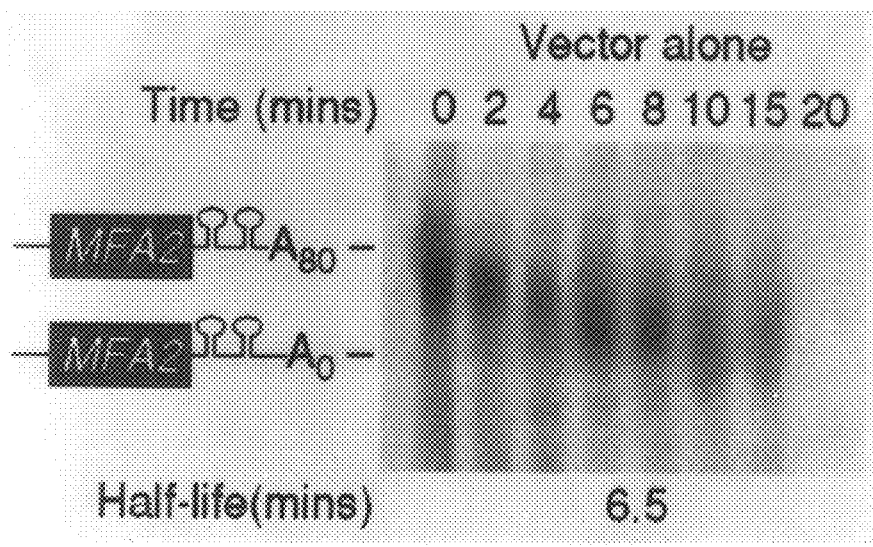
FIG. 3C is a quantitation of average poly(A) tail length over time.

FIG. 3A shows RNA prepared from strain containing MS2/Pab1p. FIG. 3B shows RNA prepared from strain containing the protein vector. FIG. 3C is a quantitation of average poly(A) tail length over time.

Although the MFA2 mRNA bearing MS2 recognition sites was stabilized approximately four-fold by the MS2/Pab1p fusion, its rate of deadenylation was not affected (FIGS. 3A and 3B). The reporter mRNA lost its poly(A) tail at a rate of 10±2 adenosine residues per minute vs. 8±1 adenosine residues in the presence of MS2/Pab1p (FIG. 3C). Intriguingly, the MFA2 reporter was stabilized in latter time points when MS2/Pab1p was tethered to the 3' UTR, although most of the transcript maintained little if any poly(A) tail (FIG. 3A, 8 to 20 minutes).

These results suggest that the MS2/Pab1p fusion stabilizes the mRNA without affecting deadenylation rate. Further, the data suggest that the presence of tethered Pab1p stabilizes an mRNA that has had its tail largely, or completely, removed.

4. Tethered Pab1p stabilizes mRNAs that never receive a tail

Figure 4A:
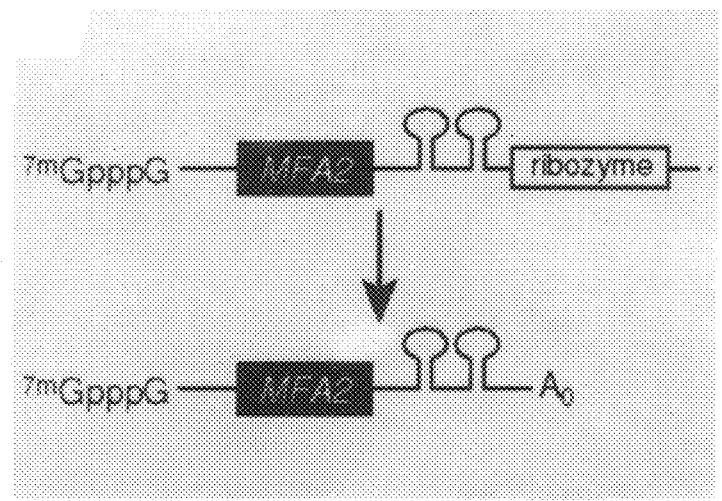
FIG. 4A is a diagram outlining the overall strategy of the experiment.

To test directly whether tethered Pab1p can stabilize an mRNA lacking a tail, we created mRNAs that did not receive poly(A) in vivo by inserting a self-cleaving ribozyme sequence into the pre-mRNA (FIG. 4A). The ribozyme was derived from Hepatitis δ Virus (HDV) ribozyme, and has been shown previously to function in yeast (Quadt, 1995).

A series of control experiments demonstrated that the ribozyme functioned as expected in vivo. FIG. 4 demonstrates that tethered Pab1p stabilizes mRNAs that do not receive a tail.

FIG. 4A is a diagram of the experimental strategy. The HDV self-cleaving ribozyme was inserted into the 3' UTR of MFA2/MS2 RNA, yielding an mRNA without a poly(A) tail ($A_0$) in vivo.

Figure 4B:
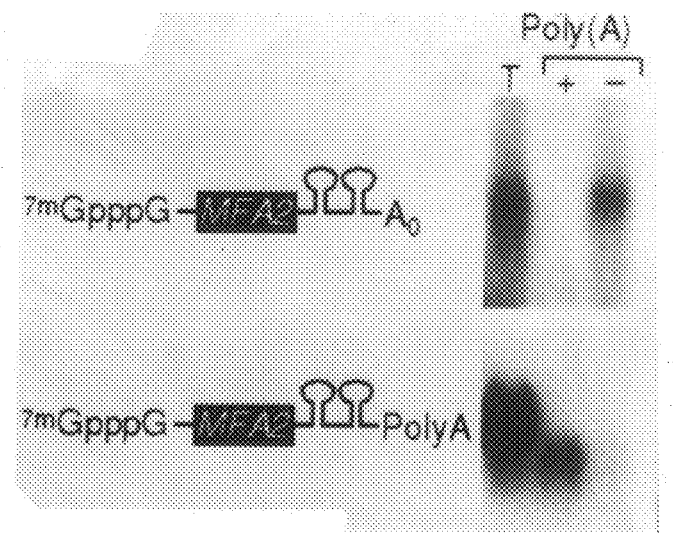
FIG. 4B compares RNAs extracted from cells carrying the ribozyme-containing construct depicted in FIG. 4A or the control plasmid.

FIG. 4B shows oligo(dT) cellulose chromatography. RNAs were extracted from cells carrying the ribozyme-containing construct depicted in (A), or the control plasmid used in previous figures. RNAs were fractionated by oligo (dT) cellulose chromatography, then analyzed by Northern blotting. The ribozyme-containing RNA is not retained by the column, while the control RNA is retained. "T", total RNA prior to fractionation; "+", retained by the column; "−", not retained by the column.

Figure 4C:
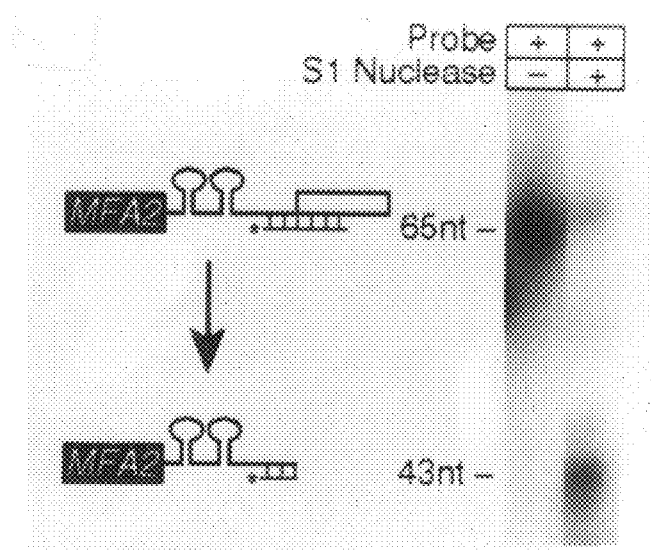
FIG. 4C is an S1 clease analysis.

FIG. 4C shows S1 nuclease analysis. The 3'-end of mRNA prepared from a strain carrying the ribozyme-containing RNA was determined by S1 nuclease mapping. The position of undigested probe (65 nucleotides) and of the protected species (43 nucleotides) are shown. The prominent 3' terminus lies at the expected position for ribozyme cleavage.

Figure 4D:
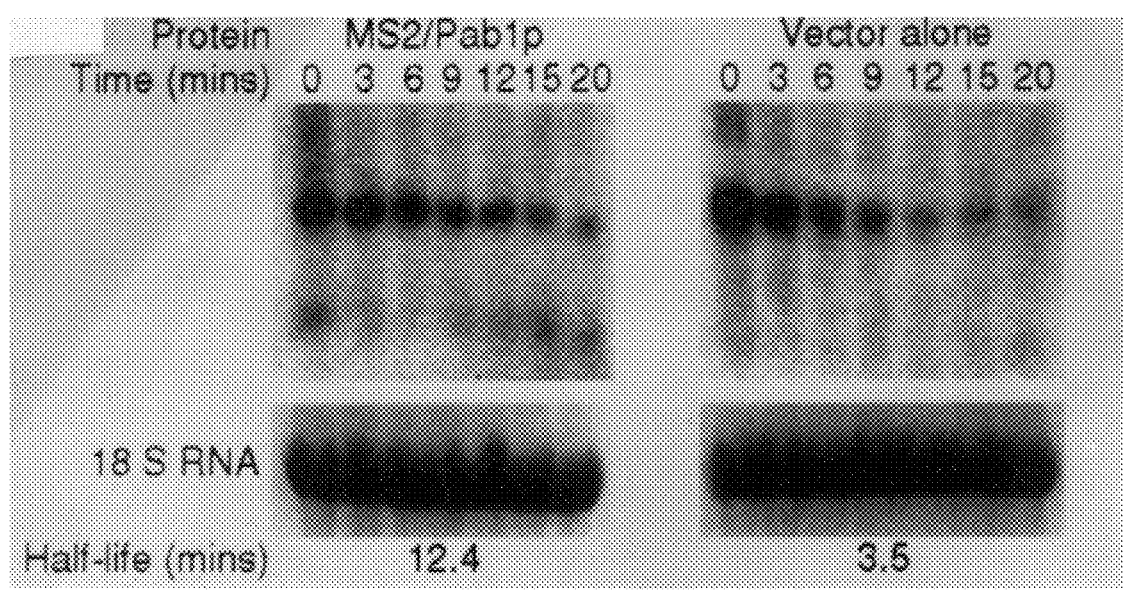
FIG. 4D is a transcriptional pulse-chase experiment and Northern blotting.

FIG. 4D shows decay of ribozyme-cleaved RNA by a transcriptional pulse-chase experiment and Northern blotting. The turnover rate of ribozyme-cleaved reporter mRNAs was determined in strains with (left) or without (right) MS2/Pab1p. Time (in minutes) following transcriptional repression are given directly above each panel; half-lives are presented below.

FIG. 4E is the quantitation of results in FIG. 4. Amounts of mRNA were normalized to the level of 18S rRNA, shown below each lane in Panel (D).

The ribozyme generated mRNAs of the predicted length in Northern blots (FIG. 4B); further, as expected, these mRNAs lacked poly(A), as they were not retained by oligo(dT) cellulose (FIG. 4B, top), while mRNAs generated by "normal" mRNA 3' processing were retained (FIG. 4B, bottom). In addition, nuclease S1 mapping experiments demonstrated that the 3' termini generated by ribozyme cleavage were within three nucleotides of the sites predicted (FIG. 4C). To ensure that cleavage occurred in vivo and not during extraction of the RNA, care was taken to prevent ribozyme cleavage during RNA preparation.

These precautions included extracting and storing RNA at low pH and in presence of EDTA (Donahue, 1997). To determine directly the extent of ribozyme cleavage during preparation, a radiolabeled in vitro transcript containing the HDV ribozyme was added to pelleted yeast cells prior to RNA extraction, then carried out through the usual protocol. The labeled RNA remained uncleaved, as shown previously (Donahue, 1997; data not shown). We deduce that the ribozyme cleaved in vivo to form non-polyadenylated 3' termini.

The non-polyadenylated MFA2/MS2 mRNA produced by the ribozyme is unstable, exhibiting a half-life of approximately 3 minutes (FIG. 4D and 4E). The presence of the MS2/Pab1p fusion protein stabilized the mRNA four-fold. We conclude that mRNA stabilization by tethered Pab1p does not require the presence of a poly(A) tail.

5. Tethered Pab1p does not prevent decay through mRNA surveillance

The presence of a premature nonsense codon triggers rapid mRNA decay without deadenylation, through a process termed mRNA surveillance (Pulak, 1993). To determine whether tethered Pab1p could prevent degradation through the mRNA surveillance pathway, we examined the stability of a PGK1 transcript carrying a nonsense mutation and bearing MS2 binding sites in its 3' UTR. The presence of the nonsense mutation greatly accelerates degradation of this normally stable transcript, reducing its half-life from 35 minutes to 4 minutes (Muhlrad, 1994). FIG. 5 demonstrates that tethered Pab1p does not prevent decay through mRNA surveillance.

Figure 5A:
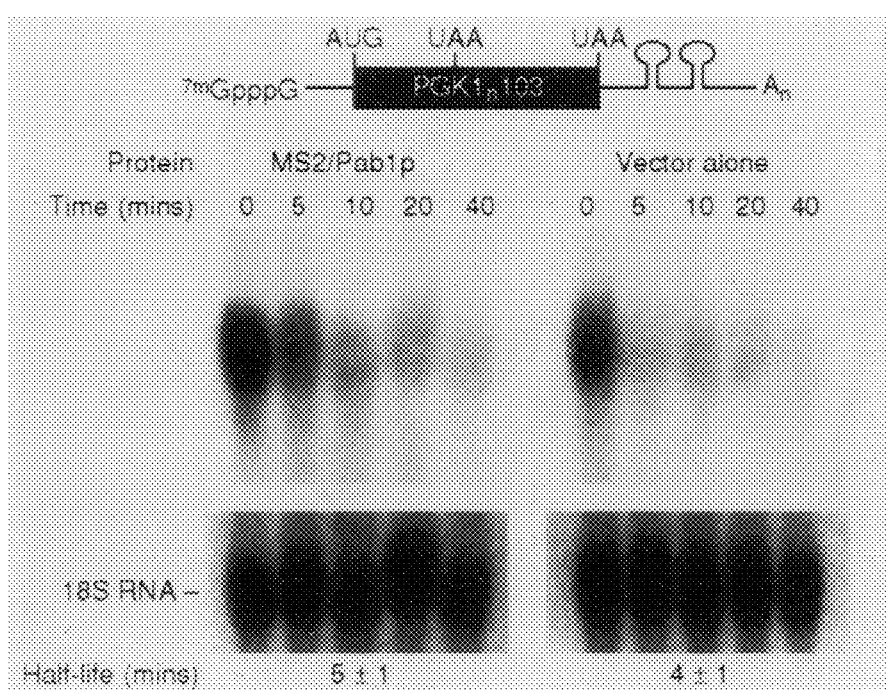
FIG. 5A diagrams a transcriptional pulse-chase experiment and Northern blotting.

FIG. 5A shows decay of nonsense mutant-containing PGK1 mRNA in a transcriptional pulse-chase experiment and Northern blotting. Stability of a PGK1/MS2 transcript harboring a non-sense mutation at position 103 was assayed in cells expressing MS2/Pab1p (left) or vector alone (right). Time (in minutes) following transcriptional repression are given above each lane; half-lives are presented below.

FIG. 5B shows quantitation of results. Amounts of mRNA were normalized to the level of 18S rRNA, shown below each lane in Panel (A).

Transcriptional pulse-chase analysis demonstrated that the presence of tethered Pab1p did not significantly stabilize the mutant mRNA (FIGS. 5A and 5B). These results strongly suggest that tethered Pab1p stabilizes only mRNAs whose decay is normally deadenylation-dependent.

6. Translation is required for tethered Pab1p to stabilize mRNA mRNA decay and translation are linked in vivo (Jacobson, 1996), and Pab1p may be essential in both processes (Hatfield, 1996; Sachs, 1989). To determine whether mRNA stabilization by tethered Pab1p requires translation of the reporter, we prepared an MFA2 transcript containing a 11 base stem loop stabilized by a UUCG tetraloop (SL-MFA2) in its 5' UTR, as well as tandem MS2 binding sites in its 3' UTR. The presence of the secondary structure in the 5' UTR reduces translation to less than 1% that of the normal mRNA (Beelman, 1994).

Figure 6A:
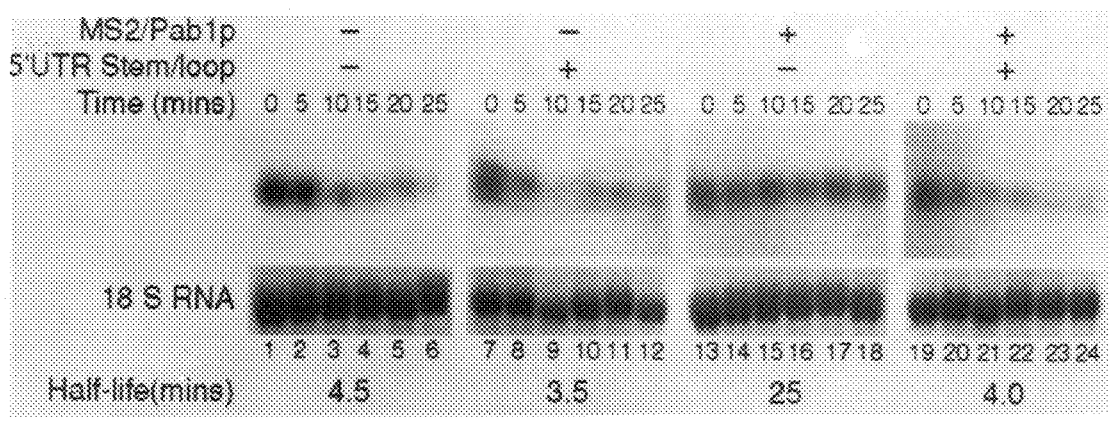
FIG. 6A is a transcriptional pulse-chase and Northern blotting analysis showing decay of MFA2/MS2 RNA bearing a stem loop in its 5' UTR.

FIG. 6 demonstrates that translation is required in cis. FIG. 6A shows decay of MFA2/MS2 mRNA bearing a stem-loop in its 5' UTR, analyzed by transcriptional pulse-chase and Northern blotting. The turnover rate of the MFA2/MS2 mRNA with or without the stem-loop in its 5' UTR was determined in strains expressing (lanes 13–18 and lanes 19–24) or lacking (lanes 1–6 and lanes 7–12) MS2/Pab1p. Time (in minutes) following transcriptional repression are given above each lane; half-lives are presented below.

FIG. 6B shows quantitation of results. Amounts of mRNA were normalized to the level of 18S rRNA, shown below each lane in Panel (A).

The presence of the 5' UTR stem-loop structure had no significant effect on mRNA stability in the absence of MS2/Pab1p (FIG. 6A, lanes 1–6 vs. 7–12). In contrast, however, the presence of the 5' stem-loop entirely abrogated stabilization by tethered Pab1p, reducing the half-life from 22 to 4.5 minutes (FIG. 6A, lanes 13–18 vs. 19–24). We infer that translation is required for stabilization by Pab1p.

7. RRM domains 3 and 4 plus two-thirds of the C-terminus are sufficient to stabilize mRNA Pab1p consists of four evolutionary conserved RNA Recognition motifs (RRMs) located at the N terminus, with a divergent 180 amino acid proline rich carboxy terminus. It has been well documented that RRM domains 1 and 2 bind to the poly(A) tail, while domains 3 and 4 bind poly(G) and poly(U) (Nietfeld, 1990; Burd, 1991; Kuhn, 1996; Deardorff, 1997). The tethered function approach allowed us to determine the regions of Pab1p required for mRNA stabilization without overriding complications of cell viability. The various deletions constructed were moved to MS2 coat protein and introduced into yeast carrying the MS2 reporter.

Figure 7A:
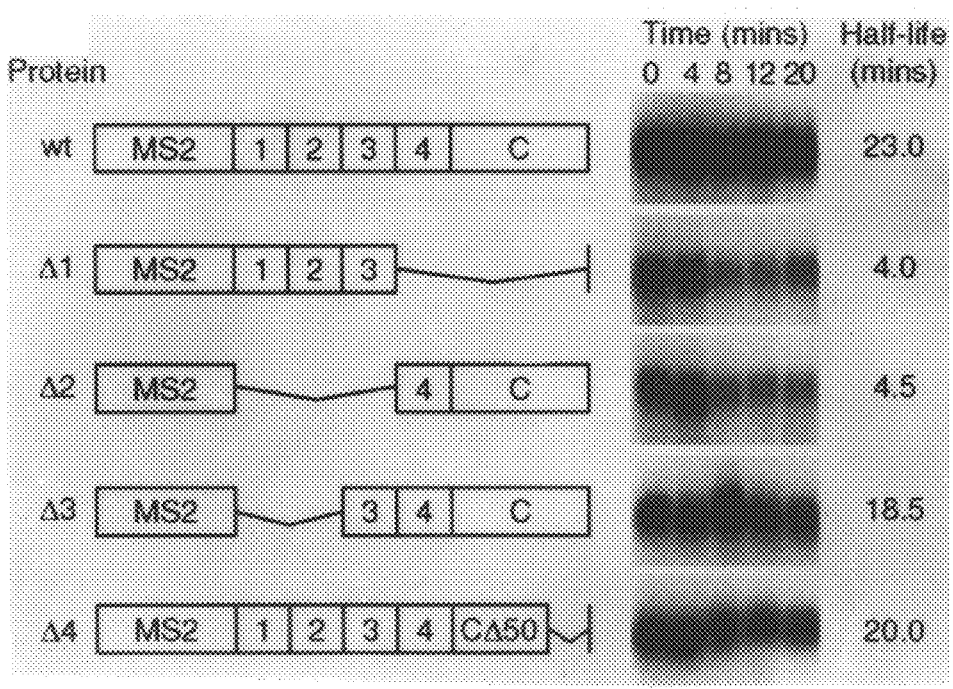
FIG. 7A is a transcriptional pulse-chase analysis.

FIG. 7 demonstrates mRNA stabilization and poly(A) binding by Pab1p are genetically separable. FIG. 7A shows decay of MFA2/MS2 mRNA in strains carrying MS2/Pab1p, analyzed by the transcriptional pulse-chase protocol. The structure of each deletion form of MS2/Pab1p is depicted to the left. Each RRM domain is designated by a number; C designates the C-terminal portion of Pab1p, CΔ50 lacks the last 50 amino acids of Pab1p. Time (in minutes) following transcriptional repression are given above each lane. Half-lives are presented to the right of the panel.

FIG. 7B shows quantitation of results. Amounts of mRNA were normalized to the level of 18S rRNA.

Figure 7C:
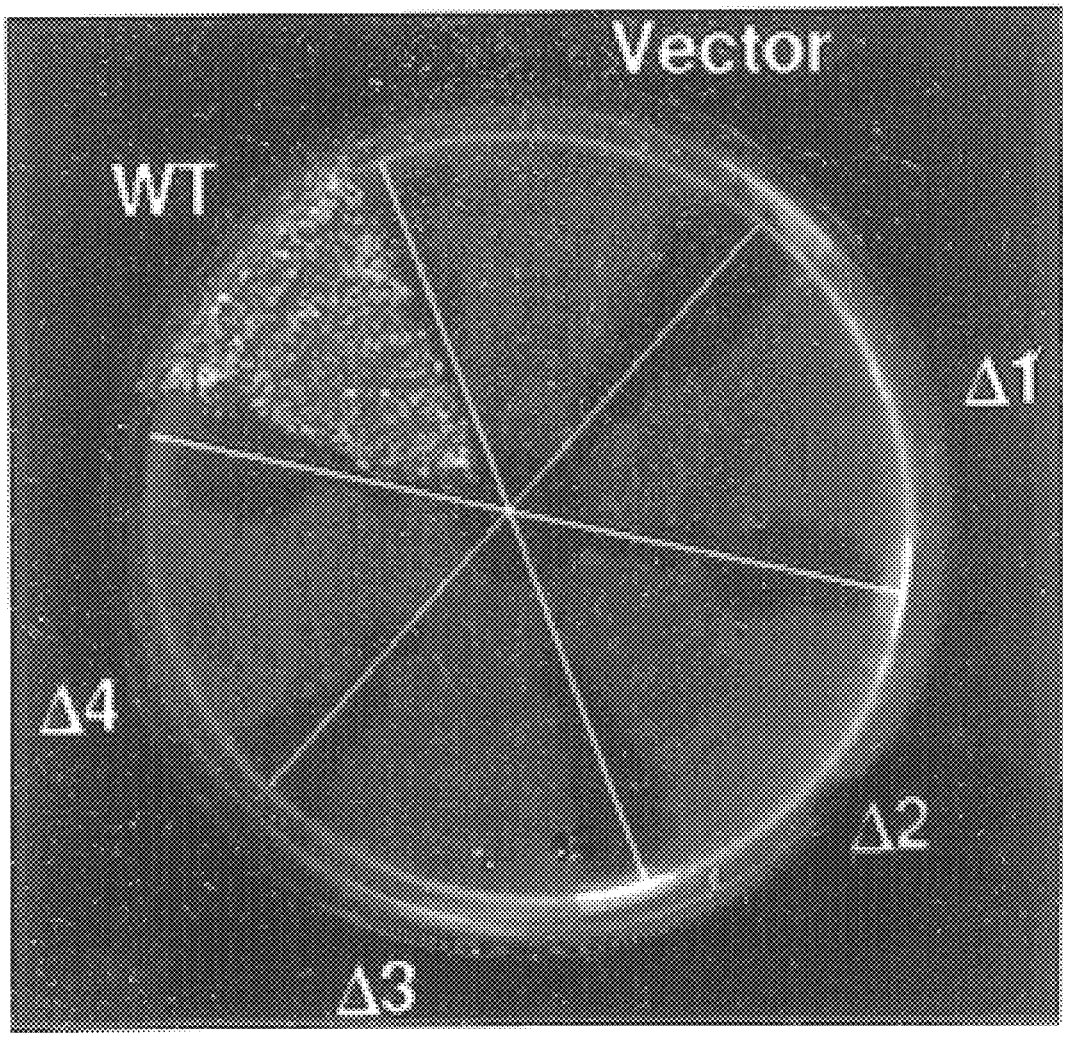
FIG. 7C is a 5-FOA selection plate.

FIG. 7C demonstrates that only full-length MS2/Pab1p complements the essential functions of Pab1p in vivo. The ability of plasmids carrying each form of MS2/Pab1p depicted in FIG. 7A to support cell growth in a strain lacking a functional PAB1 gene was determined using a plasmid shuffle assay. The assay was performed as described in Materials and Methods, and in the text (FIG. 1B). Only the wild-type construct complements a pab1Δ mutation following 5-FOA selection against a plasmid bearing both the URA3 and PAB1 gene. Based on these experiments, domain 1 and 2 were found to be dispensable for tethered Pab1p's stability function (FIG. 7). While the combination of 3 and 4 plus 130 amino acids of the C-terminus are sufficient to stabilize the MFA2/MS2 reporter (FIG. 7). These results make the point that one can analyze biological function even when the part of the protein required for binding to its natural target (in this case poly(A)) is missing.

B. Discussion

The results presented here demonstrate that Pab1p can stabilize an mRNA in the absence of the poly(A) tail, and without the regions of the protein that bind specifically to poly(A). We conclude that poly(A) s function in mRNA stability is primarily, if not entirely, to tether Pab1p to the 3' end of mRNA. Furthermore, the ability of Pab1p to stabilize an mRNA requires that the mRNA be translated, suggesting that Pab1p may act though the translational machinery to achieve its effects on stability.

Two lines of evidence establish that tethered Pab1p can stabilize an mRNA independent of the presence of a poly(A) tail. First, tethered Pab1p does not affect the deadenylation rate of mRNAs formed through the normal mRNA 3' end formation pathway; rather, it stabilizes molecules that have undergone complete, or nearly complete, deadenylation. Second, tethered Pab1p stabilizes an mRNA that has never had a poly(A) tail, in which the 3' terminus was formed by ribozyme cleavage. These two assays may reflect the same cellular function of Pab1p. On the other hand, the stabilization of initially polyadenylated and of ribozyme-cleaved mRNAs might occur through overlapping but distinct mechanisms. For example, Pab1p might be required for transport of the ribozyme-generated mRNA from the nucleus (Huang and Carmichael, 1996). Escape from the nucleus might then permit stabilization.

Our results imply that the sole function of deadenylation is the simple elimination of Pab1p binding sites: if they are effectively restored through the insertion of MS2 sites and an MS2/Pab1p chimera, then mRNAs without poly(A) become stable. Deadenylation rates vary among mRNAs, and are often controlled by sequences in the 3' UTR (Muhlrad and Parker, 1992; Herrick and Ross, 1994; Chen, et al., 1995). Such 3' UTR elements have been suggested to provide alternative binding sites for Pab1p, shuttling it off the poly(A) tail, thereby allowing deadenylation and decay (Bernstein, et al., 1989). Our data argue against such models, since Pab1p binding to the 3' UTR stabilizes, rather than destabilizes, the mRNA.

The effects of tethered Pab1p on mRNA stability require ongoing translation. Similarly, perturbation of mRNA translation stimulates rapid deadenylation and decapping of some transcripts in yeast (Muhlrad, et al., 1995; Jacobson and Peltz, 1996). In one model, a bridge linking Pab1p to eIF-4E through eIF-4G is critical both for translational stimulation and stabilization (Tarun and Sachs, 1996). However, the in vitro association between Pab1p and eIF-4G is absolutely dependent on the poly(A) tail and requires RRM2 (Tarun and Sachs, 1996; Kessler and Sachs, 1998), both of which we show here are dispensable for mRNA stabilization by Pab1p. Thus the Pab1p/eIF-4G linkage does not appear to be required for mRNA stabilization. Alternatively, other regions of Pab1p may recruit eIF-4G.

The C-terminal 50 amino acids of Pab1p are required to support viability but are not required for mRNA stabilization. These results imply that those amino acids have an essential and distinct function in vivo. This function might be to facilitate ordered binding of Pab1p to poly(A), as implied by Kuhn and Pieler (1996).

The "tethered function" assay described here, in which the function of a protein tethered to the 3' UTR is determined via its effects on an mRNA reporter, facilitates analysis of essential RNA binding proteins. For example, mutations that eliminate the vital function can be analyzed without complications of inviability. We emphasize the utility of tethering to the 3' UTR. Like promoters, 3' UTRs are relatively unconstrained in sequence, and so present similar experimental opportunities. For example, as seen here with Pab1p, proteins placed at the "wrong" location can still function.

The tethered function approach is the mirror-image of genetic strategies to detect RNA-protein interactions (e.g., MacWilliams, et al., 1993; Stripecke, et al., 1994; Harada, et al., 1996; Jain and Belasco, 1996; SenGupta, et al., 1996): it enables analysis of function without information of RNA binding, while the other assays enable analysis of RNA binding independent of function. The strategy may make it possible to search by function for proteins with roles in mRNA metabolism or control. Proteins that naturally function through the 3' UTR may be particularly accessible.

C. Materials and Methods

1. Yeast strains

Yeast strains used in this study; yN218 (MATa, rpb1-1, ura3-52, his 3, leu2), (Nonet, 1987), yJD5ts (MATa, rpb1-1, ura3-52, his4-38, leu2-1, trp1-Δ1) (Gift from Allan Jacobson, University of Massachusetts), and yAS320 (MATa, pab1::HIS3, pPAB1/URA3/CEN, his3, ura3, leu 2, ade2, trp1) (Sachs, 1987).

2. Plasmid construction

The gene for MS2 coat protein was PCRed from pLexA-MS2 (SenGupta, 1996) using the primers 5'-CAGGTCATATGGGTCCGCGGGCTTCTAACTTTAC TCAGTTCGTT-3' (SEQ ID NO: 1) and 5'-TGCTACTC GAGGGCGCTAGCGTAGATGCCGGAGTTT GCTGCG AT-3' (SEQ ID NO:2) and PFU polymerase (Stratagene). This fragment was inserted into the NdeI/XhoI site of pET-15b (Novagen) generating pET-MS2. The BamHI fragment of pAS1p68 containing the gene for Pab1p (Sachs, 1987) was inserted into the BamHI site of pET-MS2 generating pMS2-YPAB. The BamHI fragment of PYET1 containing the alcohol dehydrogenase promoter and terminator was cloned into BamHI site of Yeplac181 (Gietz, 1988), creating pANA-1. Expression of the MS2/Pab1p fusion was achieved by cloning the XbaI/SpeI fragment of pMS2-YPAB into the NheI site of pANA-1, creating pA-MPII. The plasmid expressing the MS2 coat protein dimer (pD-MS2) was created by PCR amplification of MS2 coat from pLEX-MS2-MS2 (SenGupta, 1996) and insertion into pANA-1 containing a NcoI/XhoI polylinker. The MS2/Sxl protein fusion was created by amplifying the gene for Sxl from plasmid pGEX-TEV-Sxl (Valcarcel, 1993) using oligos 5'-ATGTACGGCGCTAGCAATCCGGGTAGTAACAA TAATAATGGTGG-3' (SEQ ID NO:3) and 5'-TCAGATA AAGCTAGCAGCATCGAAATAGGGATGCGAGTTTT GGAGCG-3' (SEQ ID NO:4) and inserting into the NheI site of pA-MPII followed by XhoI/DraIII liberation of Pab1p.

The MFA2 transcript containing two tandem 3' UTR MS2 RNA binding sites was created by inserting the BglII fragment of pLTAR17 (Bardwell, 1990) into the BglII site of pRP688 (Muhlrad, 1992), creating both the MFA2/MS2 plasmid, pMM2-1, and MFA2 antisense MS2 construct, pMM2-1a. The mRNA shown in FIG. 4 was constructed by cloning the BglII fragment of pMM2-1 into the ClaI site of pRP610 (Muhlrad, 1994). The ribozyme cleaved MFA2/MS2 construct was created by inserting the Acc65I/SmaI fragment of pMM2-1 into the SnaBI/StuI site of pB2RQ39 (Quadt, 1995) creating pMM2-6.

3. MS2/Pab1p Complementation

Plasmid shuffle experiments were performed as described in (Sachs, 1987). Yeast strain yAS320 containing deletion of the PAB1 gene was suppressed by expressed Pab1p on a URA3-containing plasmid. This strain was transformed with pA-MPII, pANA-1, pD-MS2, or pA-SXL. Transformants were plated on selective media and then grown overnight in YPD. Cultures were then plated onto selective media containing the drug 5-Fluoroorotic acid. Plates were incubated at 30° C. for three days.

4. RNA preparation and analysis

Vectors containing the various reporter mRNAs were transformed into strains harboring the temperature-sensitive allele of the RNA polymerase II (rpb1-1), and transcriptional pulse-chase analysis was performed as previously described (Herrick, 1990; Muhlrad, 1992; Decker, 1993), with the following modification; cells in FIG. 5 were grown in synthetic media supplemented with 2% galactose and 2% sucrose. RNA purification and Northern analysis were performed as previously described in (Forrester, 1992), with the following modifications: 8–10 µg of total RNA were loaded onto either a 1.5% Formaldehyde agarose gel (FIGS. 2, 4 and 5B–5C) or a 4% polyacrylamide/urea gel (FIG. 3). All Northerns were probed with an antisense RNA probe to the MS2 RNA sites. RNA probes were transcribed using T3 polymerase (Epicentre) from vector pMS2-2 (SenGupta, 1996). Results from these experiments were quantitated using a Phosphoimager and ImageQuant Software (Molecular Dynamics). RNA concentrations were standardized to 18 S ribosomal RNA. Analysis of poly(A) status of mRNA was performed by oligo-dT celluloase chromatography as described in (Cleaver, 1996), and S1 nuclease mapping as described in (Goldrick, 1996) with the following exception; oligo 5'-GGAGGTGGAGATGCCATGCCGA CCCTGGTCTCTTTTAGAGATTTACAGTGTTTTCA ACACTGTACGG-3' (SEQ ID NO:5) was 3'-end labeled using terminal deoxynucleotidyl transferase (Promega), and [$\alpha$-$^{32}$P] cordycepin-5'-triphosphate.

Extracts for gel retardation and Western analysis were prepared as described in (Snyder, 1989) with the following exceptions; cells were pelleted and washed in (24 mM Hepes pH 7.6, 150 mM potassium acetate, 1.5 mM $MgCl_2$ and 5% w/v glycerol). RNA probe and competitor was generated with T7-RNA polymerase from plasmids MSA-CAT and MSCU-CAT after digestion with XbaI as described (Stripecke, 1992). Extracts were pre-treated on ice for 5 minutes with 1 mM acetic acid and 1 mM DTT. Binding reactions were performed on ice for 1 hour in a buffer containing 200 mM Tris pH 8.5, 160 mM potassium chloride, 20 mM magnesium acetate and 160 µg/mL BSA. Where indicated unlabeled competitor RNAs were added prior to the addition of the [$^{32}$P]-labeled probes. Heparin (final concentration 0.5 mg/mL) was added and followed by a 10 minute incubation. Western analysis was performed as demonstrated in (Snyder, 1989).

REFERENCES

Amrani, N., M. Minet, M. Le Gouar, F. Lacroute, and F. Wyers, "Yeast Pab1 interacts with Rna15 and participates in the control of the poly(A) tail length in vitro," *Mol. Cell. Biol.* 17:3694–3701, 1997.

Bardwell, V. and M. Wickens, "Purification of RNA and RNA-protein complexes by an R17 coat protein affinity method," *Nucl. Acids Res.* 18:6587–6594, 1990.

Bellman, C. and R. Parker, "Differential effects of translational inhibition in cis and in trans on the decay of the unstable yeast MFA2 mRNA," *J. Biol. Chem.* 269:9687–9892, 1994.

Beelman, C., A. Stevens, G. Caponigro, T. Lagrandeur, L. Hatfield, D. Fortner, and R. Parker, "An essential component of the decapping enzyme required for normal rates of mRNA turnover," *Nature* 382:642–646, 1996.

Bernstein, P., S. Peltz, and J. Ross, "The poly(A)-poly(A)-binding protein complex is a major determinant of mRNA stability in vitro," *Mol. Cell. Biol.* 9:659–670, 1989.

Burd, C., E. Matunis, and G. Dreyfuss, "The multiple NRA-binding domains of the mRNA poly(A)-binding protein have different RNA-binding activities," *Mol. Cell Biol.* 11:3419–3424, 1991.

Caponigro, G. and R. Parker, "Multiple functions for the poly(A)-binding protein in mRNA decapping and deadenylation in yeast," *Gene & Dev.* 9:2421–2432, 1995.

Caponigro, G. and R. Parker, "Mechanisms and control of mRNA turnover in *Saccharomyces cerevisiae*, " *Microbiol. Rev.* 60:233–249, 1996.

Chen, C., N. Xu, and AB. Shyu, "mRNA decay mediated by two distinct AU-rich elements from c-fos and granulocyte macrophage colony-stimulating factor transcripts: different deadenylation kinetics and uncoupling from translation," *Mol. Cell Biol.* 15:5777–5788, 1995.

Chen, C. and A. B. Shyu, "AU-rich elements: characterization and importance in mRNA degradation," *TIBS* 20:465–70, 1995.

Cleaver, O., K. Patterson and P. Krieg, "Isolation of poly-A+rna, In A laboratory guide to RNA (ed. P. Krieg), pp. 51–63. Wiley-Liss, New York, N.Y., 1996.

Deardorff, J. and A. Sachs, "Differential effects of aromatic and charged residue substitutions in the RNA binding domains of the yeast poly(A)-binding protein," *J. Mol. Biol.* 269:67, 1979.

Decker, C. and R. Parker, "A turnover pathway for both stable and unstable mRNA in yeast: evidence for a requirement for deadenylation," *Gene & Dev.* 7:1632–1643, 1993.

Donahue, C. and M. Fedor, "Kinetics of hairpin ribozyme cleavage in yeast," *RNA* 3:961–973, 1997.

Forrester, W., F. Stutz, M. Rosbash, and M. Wickens, "Defects in mRNA 3'-end formation, transcription initiation, and mRNA transport associated with the yeast mutation prp20: possible coupling of mRNA processing and chromatin structure," *Gene & Dev.* 6:1914–1926, 1992.

Gallie, D. and R. Tanguay, "Poly(A) binds to initiation factors and increases cap-dependent translation in vitro," *J. Biol. Chem.* 269:17166–17173, 1994.

Gietz, R. and A. Sugino, "New yeast—*Escherichia coli* shuttle vectors constructed with in vitro mutagenized yeast genes lacking six-base pair restriction sites," *Genes* 74:527–534, 1988.

Goldrick, M., D. Kessler, and M. Winkler, "Analysis by nuclease protection. In A laboratory guide to RNA (ed. P. Krieg), pp. 105–131. Wiley-Liss, New York New, N.Y., 1996.

Gray, N. K., S. Quick, B. Goossen, A. Constable, H. Hirling, L. C. Kuhn, L. C. Kuhn, M. W. Hentze, "Recombinant iron-regulatory factor functions as an iron-responsive-element-binding protein, a translational repressor and an aconitase: A function assay for translational repression and direct demonstration of the iron switch," *Eur. J. Biochem.* 218:657–667, 1993.

Harada, K., S. Martin, and A. Frankel, "Selection of RNA-binding peptides in vivo," *Nature* 380:175–179, 1996.

Hatfield, L., C. Beelman, A. Stevens, and R. Parker, "Mutation in trans-acting factors affecting mRNA decapping in *Saccharomyces cerevesiae*," *Mol. Cell. Biol.* 16:5830–5838, 1996.

Herrick, D., R. Parker, and A. Jacobson, "Identification and comparison of stable and unstable mRNAs as *Saccharomyces cerevesiae*, " *Mol. Cell. Biol.* 10:2269–2284, 1990.

Herrick, D. and J. Ross, "The half-life of c-myc mRNA in growing and serum-stimulated cells: Influence of the coding and 3' untranslated regions and role of ribosome translocation," *Mol. Cell Biol.* 14:2219–2138, 1994.

Huang, Y. and G. Carmichael, "Role of polyadenylation in nucleoplasmic transport of mRNA," *Mol. Cell. Biol.* 16:1534–1542, 1996.

Jacobson, A. and S. Peltz, "Interrelationships of the pathways of mRNA decay and translation in eukaryotic cells," *Annu. Rev. Biochem.* 65:693–739, 1996.

Jain, C. and J. Belasco, "A structural model for the HIV-1 Rev-RRE complex deduced from altered specificity Rev variants isolated by a rapid genetic strategy," *Cell* 87:115–126, 1996.

Kessler, S. and A. Sachs, "RNA recognition motif 2 of yeast Pab 1p is required for its functional interaction with eukaryotic translation initiation factor 4G," *Mol. Cell. Biol.* 18:51–57, 1998.

Kuhn, U. and T. Pieler, "Xenopus poly(A) binding protein: functional domains in RNA binding and protein-protein interaction," *J. Mol. Biol.* 256:20–30, 1996.

Keller, W., and L. Minvielle-Sebastia, "A comparison of mammalian and yeast pre-mRNA 3'-end processing," *Curr. Opin. Cell. Biol.* 9:329–336, 1997.

Lowary, P. and O. Uhlenbeck, "An RNA mutation that increases the affinity of an RNA-protein interaction," *Nucl. Acids Res.* 15:10483–10493, 1987.

Lowell, J., D. Rudner, and A. Sachs, "3'-UTR-dependent deadenylation by the yeast poly(A) nuclease," *Genes & Dev.* 6:2088–2099, 1992.

MacWilliams, M., D. Celander, and J. Gardner, "Direct genetic selection for a specific RNA-protein interaction," *Nucl. Acids Res.* 21:5754–5760, 1993.

Minvielle-Sebastia, L., P. Preker, and W. Keller, "The major yeast poly(A) binding protein functions in pre-messenger RNA 3'-end formation," *Proc. Natl. Acad. Sci.* 94:7897–7902, 1997.

Muhlrad, D., C. Decker, and R. Parker, "Deadenylation of the unstable mRNA encoded by the yeast MFA2 gene leads to decapping followed by 5'-3' digestion of the transcript," *Gene & Dev.* 8:855–866, 1994.

Muhlrad, D., C. Decker, and R. Parker, "Turnover mechanisms of the stable yeast PGK1 mRNA," *Mol. Cell. Biol.* 15:2145–2156, 1995.

Muhlrad, D. and R. Parker, "Mutations affecting stability and deadenylation of the yeast MFA2 transcript," *Genes & Dev.* 6:2100–2111, 1992.

Mulrad, D. and R. Parker, "Premature translation termination triggers mRNA decapping," *Nature* 370:578–581, 1994.

Nietfeld, W., H. Mentzel, and T. Pieler, "The Xenopus laevis poly(A) binding protein is composed of multiple functionally independent RNA binding domains," *EMBO J.* 9:3699–3705, 1990.

Nonet, M., C. Scafe, J. Sexton, and R. Young, "Eukaryotic RNA polymerase conditional mutant that rapidly ceases mRNA synthesis," *Mol. Cell Biol.* 7:1602–1611, 1987.

Pulak, R. and P. Anderson, "mRNA surveillance by the Caenorhabditis elegans smg genes," *Gene & Dev.* 7:1885–1897, 1993.

Quadt, R., M. Ishikawa. M. Janda, and P. Ahlquist, "Formation of brome mosaic virgus RNA-dependent RNA polymerase in yeast coexpression of viral proteins and viral RNA," *Proc. Natl. Acad. Sci.* 92:4892–4896, 1995.

Sachs, A., R. Davis, and R. Kornberg, "A single domain of yeast poly(A)-binding protein is necessary and sufficient for RNA binding and cell viability," *Mol. Cell. Biol.* 7:3268–3276, 1987.

Sachs, A., M. Bond, and R. Kornberg, "A single gene from yeast for both nuclear and cytoplasmic polyadenylate-binding proteins: Domain structure and expression," *Cell* 45:827–385, 1986.

Sachs, A. and R. Davis, "The poly(A) binding protein is required for poly(A) shortening and 60S ribosomal subunit-dependent translation initiation," *Cell* 58:857–867, 1989.

Sachs, A., P. Sarnow and M. Hentze, "Starting at the beginning, middle, and end: translation initiation in eukaryotes," *Cell* 89:831–838, 1997.

SenGupta, D., B. Zhang, B. Kraemer, P. Pochart, S. Fields, and M. Wickens, "A three-hybrid system to detect RNA-protein interactions in vivo," *Proc. Natl. Acad. Sci.* 93:8496–8501, 1996.

Synder, M., "Yeast SPA2 protein localizes to sites of cell growth," *J. Cell Biol.* 108:1419–1429, 1989.

Stripecke, R. and M. Hentze, "Bacteriophage and spliceosomal proteins function as position-dependent cis/trans repressors of mRNA translation in vitro," *Nucl. Acids Res.* 20:5555–5564, 1992.

Stripecke, R., C. Oliveira, J. McCarthy, and M. Hentze, "Proteins binding to 5' untranslated region sites: a general mechanism for translational regulation of mRNAs in human and yeast cells," *Mol. Cell Biol.* 14:5898–5909, 1992.

Tarun, S. and A. Sachs, "Association of the yeast poly(A) tail binding protein with translation initiation factor eIF-4G," *EMBO J.* 15:7168–7177, 1996.

Valcarcel, J., R. Singh, P. Zamore, and M. Green, "The protein Sex-lethal antagonizes the splicing factor U2AF to regulate alternative splicing of transformer pre-mRNA," *Nature* 362:171–175, 1993.

Wickens. M., P. Anderson, and R. J. Jackson, "Life and death in the cytoplasm: messages from the 3'-end," *Curr. Opin. Genet. Dev.* 7:220–232, 1997.

Witherell, G., J. Gott, and O. Uhlenbeck, "Specific interaction between RNA phange coat proteins and RNA," *Prog. Nucl. Acids. Res. & Mol. Biol.* 40:185–220, 1991.

We claim:

1. A method for determining the function of a test protein comprising the steps of
   (a) fusing the test protein to an RNA-binding protein, whereby a fusion protein is created,
   (b) exposing the fusion protein to a recombinant reporter mRNA molecule in yeast under conditions suitable for the binding of the fusion protein to the reporter mRNA, wherein the RNA molecule comprises a binding site for the RNA-binding protein in the 3' untranslated region and whereby the fusion protein is bound to the reporter mRNA, and
   (c) observing the properties of the reporter mRNA and correlating the properties with test protein function.

2. The method of claim 1 wherein the fusion protein is obtained by translation of a chimeric gene sequence encoding the test protein and the RNA-binding protein in tandem.

3. The method of claim 1 wherein the level of reporter mRNA in step (c) decreases.

4. The method of claim 1 wherein the level of reporter mRNA in step (c) increases.

5. The method of claim 1 wherein the RNA-binding protein is MS2 coat protein.

6. The method of claim 5 wherein the binding site of step (c) comprises the MS2 binding site.

7. The method of claim 1 wherein the observation of step (c) is a measurement of mRNA half-life or translation.

8. The method of claim 1 wherein the observation of step (c) is a detection of protein produced by the reporter mRNA.

9. The method of claim 1 wherein the observation of step (c) is the localization of protein produced by the reporter mRNA.

10. The method of claim 1 additionally comprising the step of adding a candidate inhibitor compound to step (b).

11. The method of claim 1 additionally comprising the step of adding a candidate enhancer compound to step (b).

12. The method of claim 10 wherein the compound is selected from the group consisting of proteins or peptides.

13. The method of claim 11 wherein the compound is selected from the group consisting of proteins or peptides.

14. The method of claim 1 wherein the reporter mRNA is MFA2 RNA.

15. The method of claim 1 wherein step (a) comprises creating a library of test proteins fused to known RNA binding proteins.

16. The method of claim 1 wherein step (b) comprises exposing the fusion protein to a library of recombinant reporter mRNA molecules.

17. A tethered molecular structure, comprising a recombinant reporter mRNA comprising an RNA-binding protein binding site in the 3' UTR of the reporter mRNA, and a fusion protein, comprising a test protein and an RNA-binding protein, wherein the RNA-binding protein is bound to the RNA protein binding site.

18. The structure of claim 17 wherein the RNA-binding protein is MS2 and the RNA-binding site is the MS2 binding site.

19. The structure of claim 17 wherein the recombinant reporter mRNA comprises MFA2 RNA.

* * * * *

UNITED STATES PATENT AND TRADEMARK OFFICE
CERTIFICATE OF CORRECTION

PATENT NO.    : 5,985,575

DATED         : November 16, 1999

INVENTOR(S)   : Marvin P. Wickens, et al.

Page 1 of 2

It is certified that error appears in the above-identified patent and that said Letters Patent is hereby corrected as shown below:

Column 1, line 10, remove "Not applicable" and insert --This invention was made with United States government support awarded by the following agencies: NIH Grant Nos. GMC50942 and GMC31892. The United States has certain rights in this invention.--

Column 3, Line 40:

"MRNA"    should be    --mRNA--

Column 4, Line 53:

"MRNA"    should be    --mRNA--

Column 5, Line 11:

"MRNA"    should be    --mRNA--

UNITED STATES PATENT AND TRADEMARK OFFICE
CERTIFICATE OF CORRECTION

PATENT NO. : 5,985,575
DATED : November 16, 1999
INVENTOR(S) : Marvin P. Wickens, et al.

It is certified that error appears in the above-identified patent and that said Letters Patent is hereby corrected as shown below:

Column 10, Line 31:

"Pablip" should be --Pab1p--

Signed and Sealed this

Twenty-second Day of August, 2000

*Attest:*

Q. TODD DICKINSON

*Attesting Officer*   *Director of Patents and Trademarks*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 44 base pairs
      (B) TYPE: nucleic acid
      (C) STRANDEDNESS: single
      (D) TOPOLOGY: linear (ii) MOLECULE TYPE: Oligonucleotide -continued (xi) SEQUENCE DESCRIPTION: SEQ ID NO:1:

CAGGTCATAT GGGTCCGCGG GCTTCTAACT TTACTCAGTT CGTT          44

(2) INFORMATION FOR SEQ ID NO:2:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:2:

TGCTACTCGA GGGCGCTAGC GTAGATGCCG GAGTTTGCTG CGAT          44

(2) INFORMATION FOR SEQ ID NO:3:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:3:

ATGTACGGCG CTAGCAATCC GGGTAGTAAC AATAATAATG GTGG          44

(2) INFORMATION FOR SEQ ID NO:4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:4:

TCAGATAAAG CTAGCAGCAT CGAAATAGGG ATGCGAGTTT TGGAGCG       47

(2) INFORMATION FOR SEQ ID NO:5:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:5:

GGAGGTGGAG ATGCCATGCC GACCCTGGTC TCTTTTAGAG ATTTACAGTG TTTTTCAACA    60

CTGTACGG                                                            68